United States Patent
Mato Sabat

(10) Patent No.: US 11,541,181 B2
(45) Date of Patent: Jan. 3, 2023

(54) STERILE SYRINGE COMPRISING A NON-SLIDING SEAL

(71) Applicant: Biosafe S.A., Eysins (CH)

(72) Inventor: Pau Mato Sabat, Eysins (CH)

(73) Assignee: Biosafe S.A., Eysins (CH)

( * ) Notice: Subject to any disclaimer, the term of this patent is extended or adjusted under 35 U.S.C. 154(b) by 342 days.

(21) Appl. No.: 16/758,555

(22) PCT Filed: Oct. 25, 2018

(86) PCT No.: PCT/EP2018/079348
§ 371 (c)(1),
(2) Date: Apr. 23, 2020

(87) PCT Pub. No.: WO2019/081678
PCT Pub. Date: May 2, 2019

(65) Prior Publication Data
US 2020/0345940 A1   Nov. 5, 2020

(30) Foreign Application Priority Data

Oct. 26, 2017 (GB) ..................................... 1717644

(51) Int. Cl.
*A61M 5/31* (2006.01)
*A61M 5/315* (2006.01)
*A61L 2/20* (2006.01)

(52) U.S. Cl.
CPC ........... *A61M 5/3145* (2013.01); *A61L 2/206* (2013.01); *A61M 5/3135* (2013.01);
(Continued)

(58) Field of Classification Search
CPC .............. A61M 5/3135; A61M 5/3145; A61M 5/31501; A61M 5/31513;
(Continued)

(56) References Cited

U.S. PATENT DOCUMENTS 4,177,149 A * 12/1979 Rosenberg ......... B01D 19/0031
210/500.21
8,777,906 B1   7/2014 Gray
(Continued)

FOREIGN PATENT DOCUMENTS

CN     201020107 Y     2/2008
CN     201022886 Y     2/2008
(Continued)

OTHER PUBLICATIONS

PCT International Search Report and Written Opinion for PCT Application No. PCT/EP2018/079348 dated Jan. 7, 2019 (8 pages).
(Continued)

*Primary Examiner* — Nathan R Price
*Assistant Examiner* — Justin L Zamory
(74) *Attorney, Agent, or Firm* — Eversheds Sutherland (US) LLP

(57) ABSTRACT

The invention discloses a sterile syringe (100) comprising a barrel (1) having internal surfaces (2), a plunger (3) movable within the barrel, a non-sliding seal (7) between the barrel and the plunger defining a sealed volume (8) and at least one filter (9) allowing only filtered gases to enter the sealed volume such that the syringe maintains its sterility even after several uses. The filters could be positioned on different locations on the syringe like on the non-sliding seal, the barrel, the barrel flange or the plunger handle.

15 Claims, 6 Drawing Sheets

(52) U.S. Cl.
CPC .... *A61M 5/31501* (2013.01); *A61M 5/31513* (2013.01); *A61L 2202/23* (2013.01); *A61M 2005/3121* (2013.01); *A61M 2005/3151* (2013.01); *A61M 2205/02* (2013.01)

(58) Field of Classification Search
CPC .. A61M 2005/3121; A61M 2005/3151; A61M 2205/02

See application file for complete search history.

(56) References Cited

U.S. PATENT DOCUMENTS

| | | | |
|---|---|---|---|
| 2003/0097115 A1 | 5/2003 | Gruenberg | |
| 2003/0139706 A1 | 7/2003 | Gray | |
| 2011/0046604 A1 | 2/2011 | Felsovalyi et al. | |
| 2011/0124035 A1* | 5/2011 | Broadley | C12M 23/28 435/29 |
| 2012/0265140 A1 | 10/2012 | Thorne, Jr. et al. | |

FOREIGN PATENT DOCUMENTS

| | | |
|---|---|---|
| CN | 202277577 U | 6/2012 |
| CN | 205586318 U | 9/2016 |
| JP | 09313606 A | 12/1997 |
| JP | 2005198875 A | 7/2005 |
| WO | 2009/115009 A1 | 9/2009 |

OTHER PUBLICATIONS

Great Britain Search Report for GB Application No. 1717644.7 dated Mar. 14, 2018 (4 pages).

* cited by examiner

STERILE SYRINGE COMPRISING A NON-SLIDING SEAL

CROSS REFERENCE TO RELATED APPLICATIONS

This application claims the priority benefit of PCT/EP2018/079348 filed on Oct. 25, 2018, which claims priority benefit of Great Britain Patent Application No. 1717644.7 filed on Oct. 26, 2017, the entire contents of which are hereby incorporated by reference herein.

TECHNICAL FIELD

The present invention relates to syringes with one or more filters.

BACKGROUND

Syringes which have a cylindrical barrel and a plunger slideable within the barrel are frequently used in healthcare settings like a hospital or a pharmacy. They are also used in pathology labs or in biopharmaceutical production labs and facilities. Syringes are used for various purposes like administering injections and infusions, measuring up fluids, drawing out fluid samples and transferring fluids between different containers.

However, most of the frequently used syringes are not designed to be sterile systems and sterility is typically lost after opening the outer packaging in which the syringe is enclosed or after just a single use. This happens because such syringes are open systems and when they are operated, the plunger and the inside surfaces of the barrel get exposed to the atmosphere. This causes the syringed fluids to come into contact with non-sterile surfaces of the syringe as they are aspirated in the barrel, thus increasing the chances of contamination in those fluids.

WO99/45851 (Harvest Technologies Corporation) describes a syringe for use in collecting and transferring physiological fluids from a non-sterile field to a sterile field where the syringe is encased in a two-part outer casing such that the syringe is held in a sterile condition. During operation of the syringe, a fluid is drawn into the sterile syringe held in the casing while in the non-sterile field. The casing is then opened to expose the syringe and the casing is held such that the syringe can be grasped by a person in the sterile field and removed from the casing, or dropped into the sterile field. Thus, the syringe once out of its casing is required to be in a sterile atmosphere to maintain the sterility of the syringe. This method is not only susceptible to human error while removing the casing but also requires a facility where a sterile room/area could be maintained.

EP1723979B1 (Sophrone Ranguin) describes a syringe where a tubular membrane is attached to the proximal end of the barrel on one side and to the proximal end of the plunger on other side to form a closed syringe such that during operation of the syringe, parts of the syringe that come in contact with the syringed fluids are not exposed to the atmosphere. This system is however, prone to inefficiencies as there is no mechanism for pressure balancing due to any change in volume of air in the closed syringe when the plunger is repeatedly pushed in and out within the barrel. Thus, after repeated use, the syringe could stop functioning properly.

There is a need for a sterile syringe that maintains sterility even when operated in a non-sterile environment and that can continue to work efficiently even with multiple use.

SUMMARY OF THE INVENTION

Invention is defined by the claims herein. Embodiments of the invention address the problems mentioned above.

One advantage of those embodiments is that the parts of the syringe that come in contact with the syringed fluids are sealed off from the non-sterile atmosphere when the syringe is operated.

Another advantage of those embodiments is that the sterility of the syringe is maintained during operation as any air entering the syringe through the filters is sterile.

Another advantage of those embodiments is that the syringe has increased efficiency during repeated use of the syringe because the air can enter in or escape out through the filters in the syringe and maintain the desired pressure within the syringe for efficient operation.

Another advantage of those embodiments is that the syringe could be operated multiple times while maintaining sterility.

Another advantage of those embodiments is that the syringe could be sterilized using sterilizing gases such as Ethylene Oxide (EtO) gas.

According to an embodiment of the invention, a flexible non-sliding seal is used between the barrel and the plunger of the syringe such that a sealed volume is created within the syringe. One or more filters are located on the syringe. The filters prevent any pathogens in the atmosphere to pass through them and into the sealed volume, only allowing gases such as EtO or sterile air to enter the sealed volume. When the plunger is completely pushed in the barrel of the syringe as is the case in a new unused sterile syringe, the non-sliding seal gets stretched. When the plunger is retracted to aspirate a volume of fluid in the barrel of the syringe, the non-sliding seal gets compressed. As the non-sliding seal of the syringe seals off those parts of the syringe that come in contact with the syringed fluids, like the inner surfaces of the barrel, from the non-sterile atmosphere, the sterility of the syringe is maintained even after repeated movement of the plunger. Further, to balance out any pressure change within the syringe caused due to changes in the sealed volume caused due to movement of the plunger, air is sucked in or expelled out through the filters located on the non-sliding seal. As the filters allow only sterile air to pass into the sealed volume, this allows the sterility to be maintained even after repeated use.

According to a method of the invention, a new unused syringe is exposed to sterilizing gas EtO. EtO enters the sealed volume of the syringe through the filters on the syringe, thus sterilizing the sealed volume in the process.

More advantages and benefits of the present invention will become readily apparent to the person skilled in the art in view of the detailed description below.

DRAWINGS

The invention will now be described in more detail with reference to the appended drawings, wherein.

DETAILED DESCRIPTION

Figure 1A:
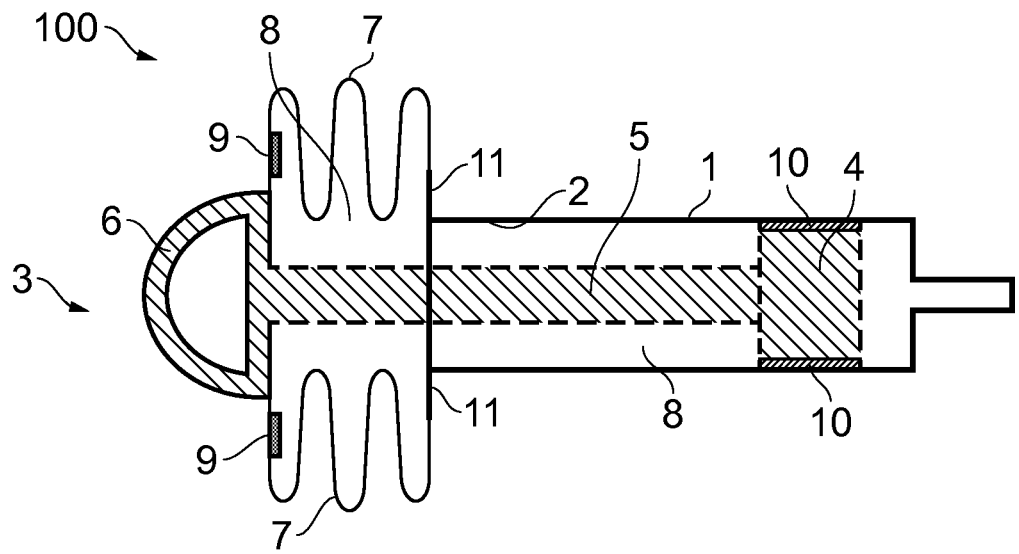
FIG. 1A shows a first side view of an exemplary syringe 100 according to a first embodiment of the invention.

FIG. 1A shows a first side view of an exemplary syringe 100 according to a first embodiment of the invention. The syringe 100 comprises a barrel 1 and a plunger 3. The barrel 1 comprises internal surfaces 2 and a flange 11 extending outwards from the periphery of a proximal end of the barrel 1. The plunger 3 comprises a piston 4, a stem 5 and a handle 6. The piston 4 of the plunger 3 is connected to the internal surfaces 2 of the barrel 1 by a sliding seal 10. The piston 4 can be moved within the barrel 1 in a linear manner using the handle 6 of the plunger 3. When the handle 6 is pulled out, the piston 4 moves towards the proximal end of the barrel 1. When the handle 6 is pushed in, the piston 4 moves towards a distal end of the barrel 1. The syringe 100 also comprises a non-sliding seal 7 attached to the barrel 1 and the plunger 3, enclosing a sealed volume 8 within the syringe 100. As shown in FIG. 1A, the non-sliding seal 7 in the first embodiment of the invention, is in the form of bellows and is attached to the flange 11 of the barrel 1 and the handle 6 of the plunger 3, enclosing the sealed volume 8 within the syringe 100. The plunger 3 is always within the sealed volume 8 making the syringe 100 a closed system. Once the closed syringe 100 is sterilized using EtO for example before a first use, the sterility is maintained within it as there is no exposure to the atmosphere, this makes repeated use of the syringe 100 possible without compromising sterility. Thus, during the operation of the syringe 100, the syringed liquids are never exposed to non-sterile surfaces. The non-sliding seal 7 is made of flexible impermeable material for example, latex, silicone or flexible plastics. The syringe 100 further comprises one or more filters 9. In the exemplary syringe of FIG. 1A, the filters 9 are located on the bellows. The filter material allows gases such as Ethylene Oxide (EtO) to enter the otherwise sealed volume 8 for the purpose of sterilisation of that volume. The filter can be made of any material which allows the transfer of such sterilising gases, but inhibits the transfer of larger sized matter, as such macromolecules, bacteria, spores, viruses and the like. Suitable filter material is for example, nylon. Suitable filters include Tyvek® brand microbial bathers which are formed from continuous, randomly oriented, high-density polyethylene (HDPE) filaments. Suitable pore size of the filters is for example 0.2 μm. The filters 9 allow entry of sterile air in the sealed volume 8 to adjust the pressure in the syringe 100 when the plunger 3 is moved within the barrel 1, thus also maintaining sterility within the syringe 100. In the first view of the exemplary syringe as illustrated in FIG. 1A, the plunger 3 is pushed in such that the piston 4 is in a first position which is nearer to the distal end of the barrel 1. When the piston 4 is in the first position, the bellows 7 are in a folded configuration.

Figure 1B:
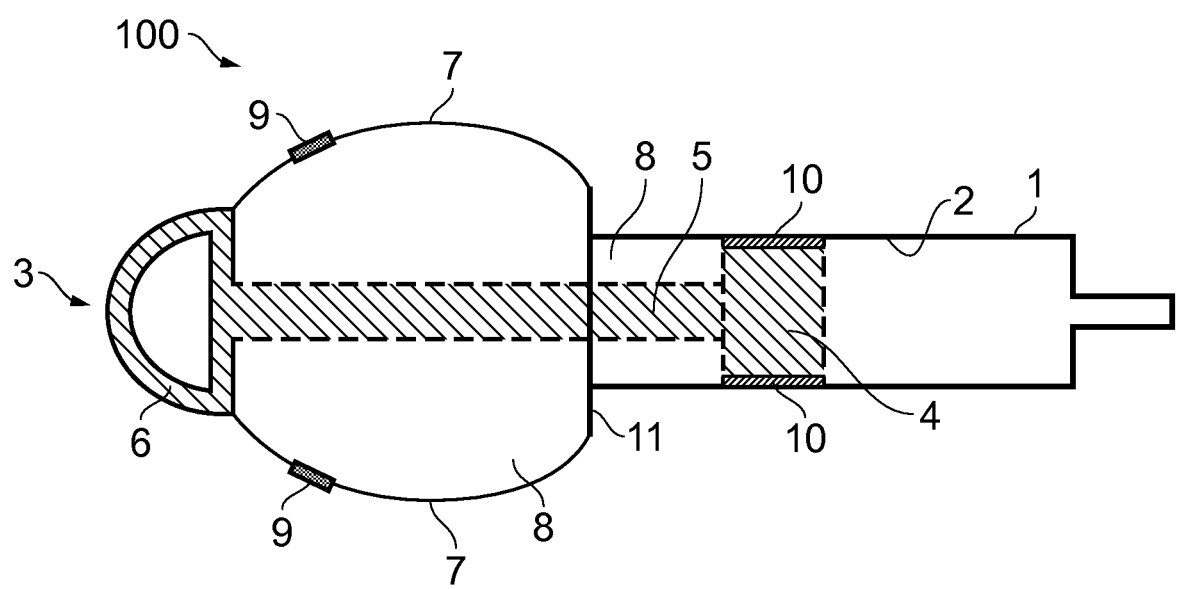
FIG. 1B shows a second side view of the exemplary syringe 100 as illustrated in FIG. 1A.

FIG. 1B shows a second side view of the exemplary syringe 100 as illustrated in FIG. 1A. The plunger 3 is pulled out such that the piston 4 is in a second position which is nearer to the proximal end of the barrel 1. When the piston 4 is moved from the first position to the second position, the air behind the piston 4 is displaced and pushed into the folds of the bellows 7 thereby inflating the bellows 7. Thus, in the second position, the bellows 7 are in an inflated configuration. Due to change in the volume of the air within the syringe 100 due to movement of the plunger 3, some air may enter or escape through the filters 9 to maintain a suitable pressure inside the syringe 100.

Figure 2A:
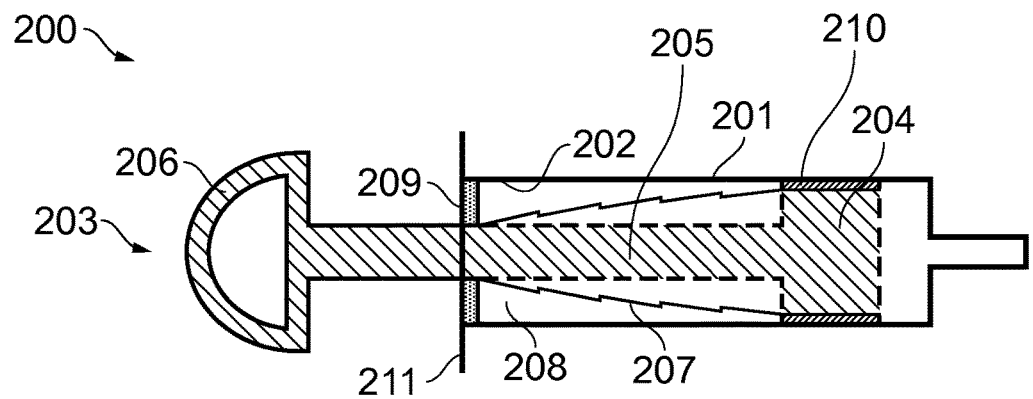
FIG. 2A shows a first side view of an exemplary syringe 200 according to a second embodiment of the invention.

FIG. 2A shows a first side view of an exemplary syringe 200 according to a second embodiment of the invention. The syringe 200 comprises a barrel 201 and a plunger 203. The barrel 201 comprises internal surfaces 202 and a flange 211 extending outwards from the periphery of a proximal end of the barrel 201. The plunger 203 comprises a piston 204, a stem 205 and a handle 206. As illustrated in FIG. 2A, the stem 205 of the plunger 203 is exposed to the atmosphere and the contaminants contained therein. The piston 204 of the plunger 206 is connected to the internal surfaces 202 of the barrel 201 by a sliding seal 210. The piston 204 can be moved within the barrel 201 in a linear manner using the handle 206 of the plunger 203. When the handle 206 is pulled out, the piston 204 moves towards the proximal end of the barrel 201. When the handle 206 is pushed in, the piston 204 moves towards a distal end of the barrel 201. The syringe 200 also comprises a non-sliding seal 207 attached to the barrel 201 and the plunger 203 in a first configuration, enclosing a sealed volume 208 within the syringe 200. As shown in FIG. 2A, the non-sliding seal 207 in the second embodiment of the invention, is in the form of a flexible telescopic membrane and is attached to the flange 211 of the barrel 201 and the piston 204 of the plunger 203, enclosing the sealed volume 208 within the syringe 200. The non-sliding seal 207 seals off the internal surfaces 202 of the barrel 201 and prevents the transfer of any contaminants picked up by the stem 205 and the piston 204 during operation of the plunger 203 during which operation the plunger 203 is exposed to the atmosphere and the contaminants contained therein. Thus, once the syringe 200 is sterilized using EtO, for example before a first use, sterility is maintained within the syringe 200. When a sterile fluid is syringed using the syringe 200, the syringed fluid comes in contact with only the sterile surfaces of the syringe 200 and thus sterility of the syringed fluid is maintained. The non-sliding seal 207 is made of flexible impermeable material for example latex, silicone or flexible plastics. The syringe 200 further comprises one or more filters 209. The filters 209 allow entry of only sterile air in the sealed volume 208 to adjust the pressure in the syringe 200 when the plunger 203 is moved within the barrel 201, thus also maintaining sterility within the syringe 200. In the exemplary syringe of FIG. 2A, the filters 209 are located on the flange 211 of the barrel 201. In the first view of the exemplary syringe 200 as illustrated in FIG. 2A, the plunger 203 is pushed in such that the piston 204 is in a first position which is nearer to the distal end of the barrel 201. When the piston 204 is in the first position, the telescopic non-sliding seal 207 is in an extended configuration.

Figure 2B:
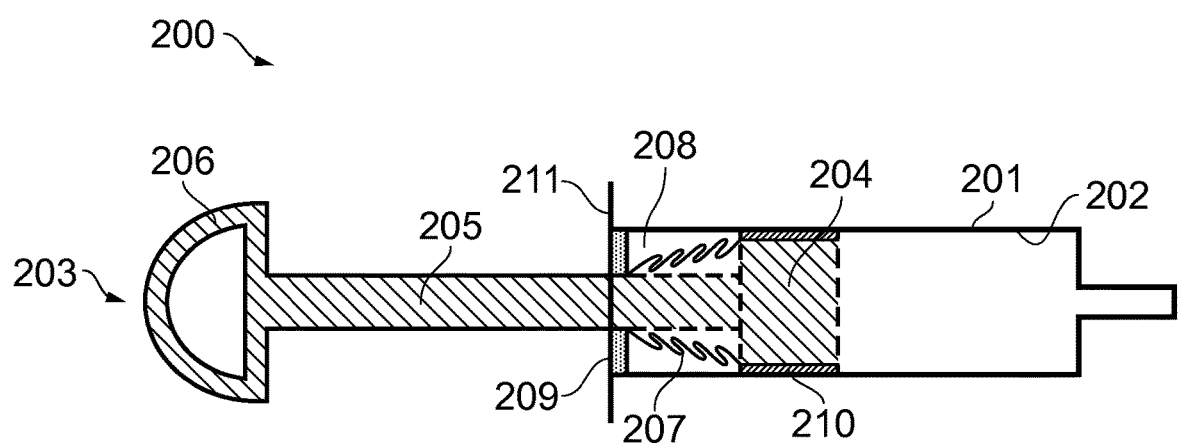
FIG. 2B shows a second side view of the exemplary syringe 200 as illustrated in FIG. 2A.

FIG. 2B shows a second side view of the exemplary syringe 200 as illustrated in FIG. 2A. The plunger 203 is pulled out such that the piston 204 is in a second position which is nearer to the proximal end of the barrel 201. When the piston 204 is moved from the first position to the second position, the non-sliding telescopic seal 207 collapses onto itself and some of the air within the sealed volume 208 is expelled out of the syringe through the filters 209 to balance the pressure within the syringe 200. Thus, in the second position, the telescopic non-sliding seal 207 is in a collapsed configuration.

Figure 3A:
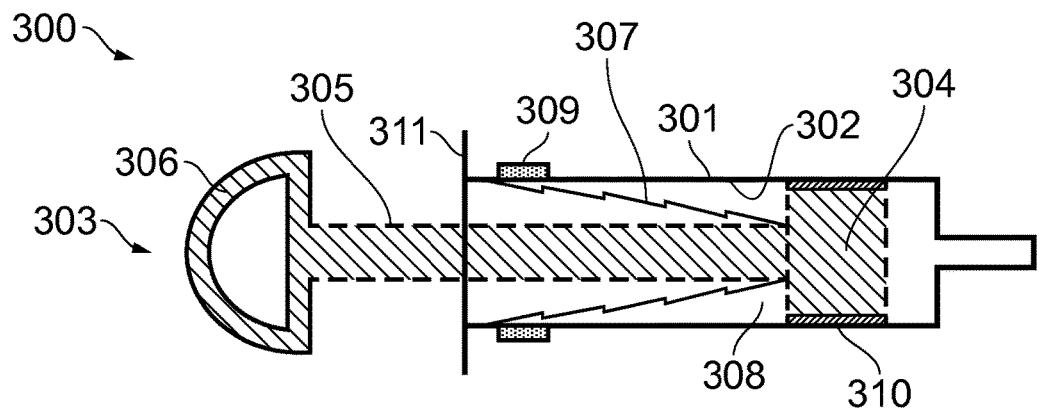
FIG. 3A shows a first side view of an exemplary syringe 300 according to a third embodiment of the invention.

FIG. 3A shows a first side view of an exemplary syringe 300 according to a third embodiment of the invention. The syringe 300 comprises a barrel 301 and a plunger 303. The barrel 301 comprises internal surfaces 302 and a flange 311 extending outwards from the periphery of a proximal end of the barrel 301. The plunger 303 comprises a piston 304, a stem 305 and a handle 306. As illustrated in FIG. 3A, the stem 305 of the plunger 303 is exposed to the atmosphere and the contaminants contained therein. The piston 304 of the plunger 306 is connected to the internal surfaces 302 of the barrel 301 by a sliding seal 310. The piston 304 can be moved within the barrel 301 in a linear manner using the handle 306 of the plunger 303. When the handle 306 is pulled out, the piston 304 moves towards the proximal end of the barrel 301. When the handle 306 is pushed in, the piston 304 moves towards a distal end of the barrel 301. The syringe 300 also comprises a non-sliding seal 307 attached to the barrel 301 and the plunger 303 in a second configuration, enclosing a sealed volume 308 within the syringe 300. As shown in FIG. 3A, the non-sliding seal 307 in the third embodiment of the invention, is in the form of a flexible telescopic sheet and is attached to the flange 311 of the barrel 301 and the stem 305 of the plunger 303, enclosing the sealed volume 308 within the syringe 300. The non-sliding seal 307 seals off the internal surfaces 302 of the barrel 301 and prevents the transfer of any contaminants picked up by the stem 305 during operation of the plunger 303 during which operation the plunger 303 is exposed to the atmosphere and the contaminants contained therein. Thus, once the syringe 300 is sterilized using EtO, for example before a first use, sterility is maintained within the syringe 300. When a sterile fluid is syringed using the syringe 300, the syringed fluid comes in contact with only the sterile surfaces of the syringe 300 and thus sterility of the syringed fluid is maintained. The non-sliding seal 307 is made of flexible impermeable material for example latex, silicone or flexible plastics. The syringe 300 further comprises one or more filters 309. The filters 309 allow entry of only sterile air in the sealed volume 308 to adjust the pressure in the syringe 300 when the plunger 303 is moved within the barrel 301, thus also maintaining sterility within the syringe 300. In the exemplary syringe of FIG. 3A, the filters 309 are located on the barrel 301. In the first view of the exemplary syringe 300 as illustrated in FIG. 3A, the plunger 303 is pushed in such that the piston 304 is in a first position which is nearer to the distal end of the barrel 301. When the piston 304 is in the first position, the telescopic non-sliding seal 307 is in an extended configuration.

Figure 3B:
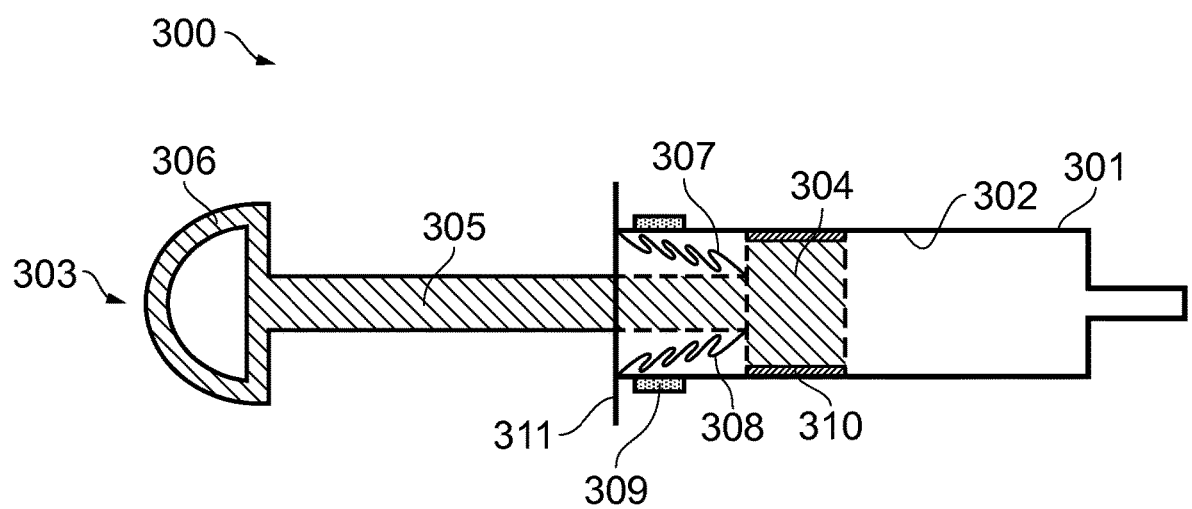
FIG. 3B shows a second side view of the exemplary syringe 300 as illustrated in FIG. 3A.

FIG. 3B shows a second side view of the exemplary syringe 300 as illustrated in FIG. 3A. The plunger 303 is pulled out such that the piston 304 is in a second position which is nearer to the proximal end of the barrel 301. When the piston 304 is moved from the first position to the second position, the non-sliding telescopic seal 307 collapses onto itself and some of the air within the sealed volume 308 is expelled out of the syringe through the filters 309 to balance the pressure within the syringe. Thus, in the second position, the telescopic non-sliding seal 307 is in a collapsed configuration.

Figure 4A:
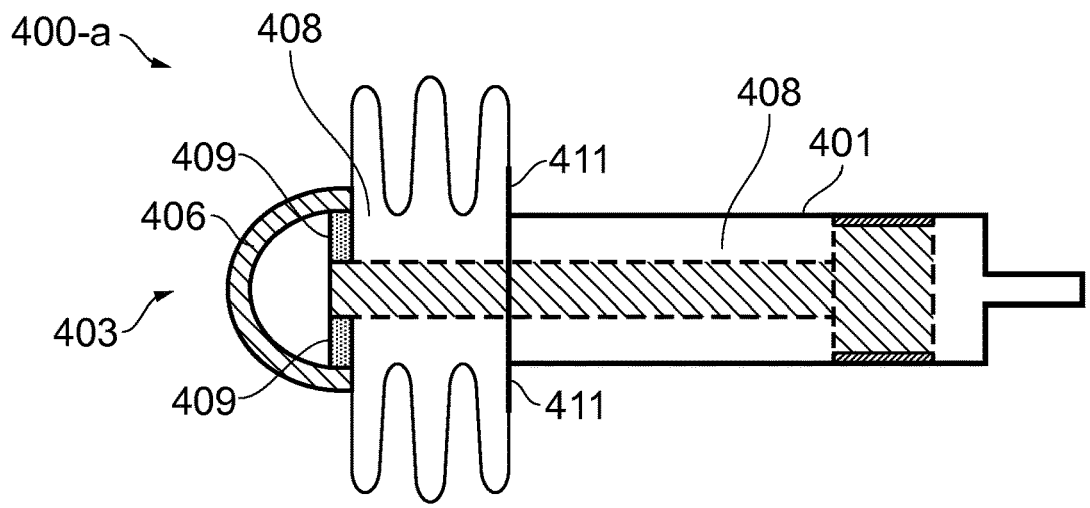
FIGS. 4A, 4B and 4C show side views of three further exemplary syringes 400-*a*, 400-*b* and 400-*c*, similar to the syringes shown in FIGS. 1A and 1B according to the first embodiment of the invention.
Figure 4B:
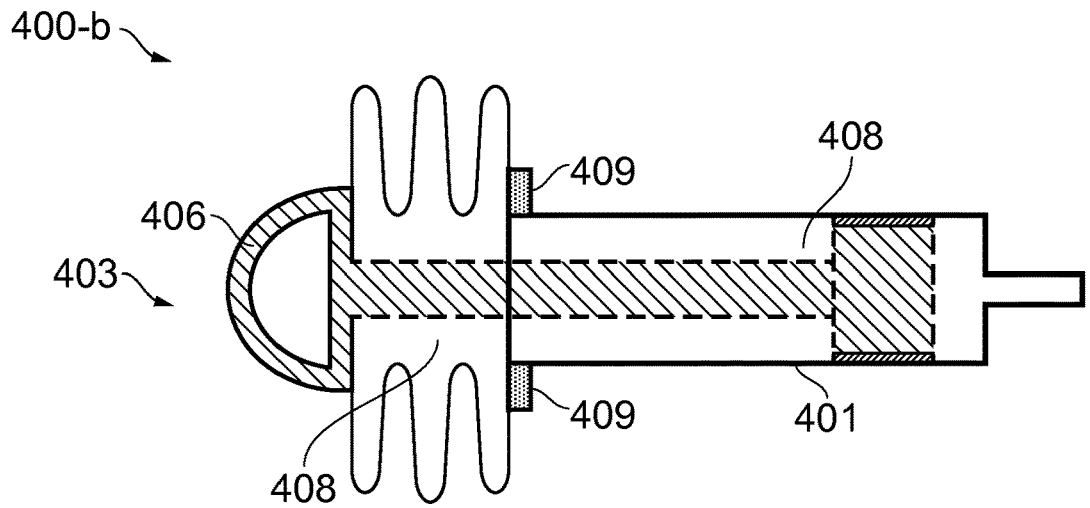
Figure 4C:
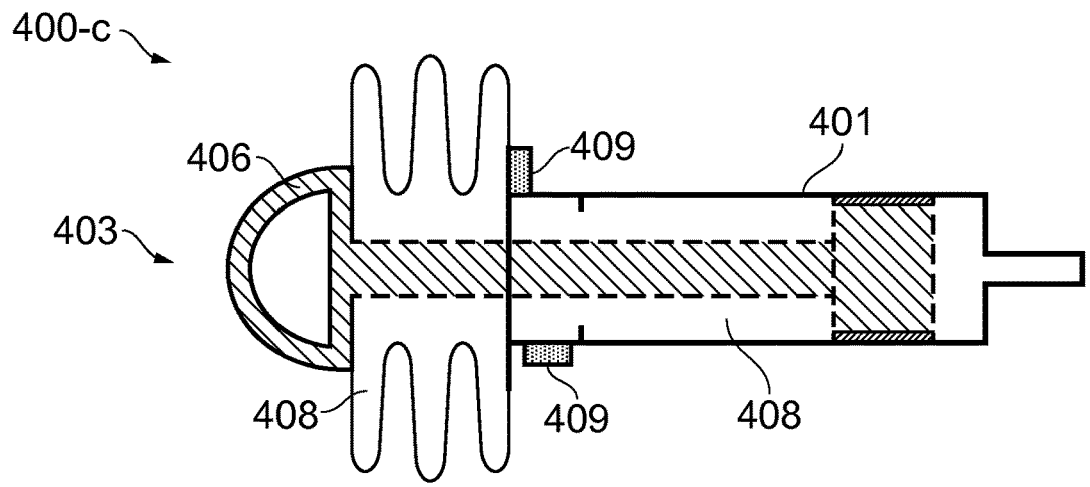

FIGS. 4A, 4B and 4C show side views of three further exemplary syringes 400-*a*, 400-*b* and 400-*c*, similar to the syringes shown in the first embodiment of the invention as described above in relation to FIGS. 1A and 1B. Each of the syringes 400-*a*, 400-*b* and 400-*c* comprise a barrel 401, a barrel flange 411, a plunger 403, a plunger handle 406, one or more filters 409 and a sealed volume 408. The syringes 400-*a*, 400-*b* and 400-*c* differ from each other in the positioning of their filters 409. Each of the filters 409 are positioned at different locations on the respective syringes such that the filters 409 are in fluid communication with the sealed volume 408 within the respective syringes and only allow sterile air or sterilizing gases such as EtO to pass through into the sealed volume 408. As illustrated in FIG. 4A, the filters 409 are located on the plunger handle 406 of the syringe 400-*a*. As illustrated in FIG. 4B, the filters 409 are located on the barrel flange 411 of the syringe 400-*b*. As illustrated in FIG. 4C, the filters 409 are located on the barrel 401 and on the barrel flange 411 of the syringe 400-*c*. The features not described are similar to those described in FIG. 1A and FIG. 1B above.

Figure 5A:
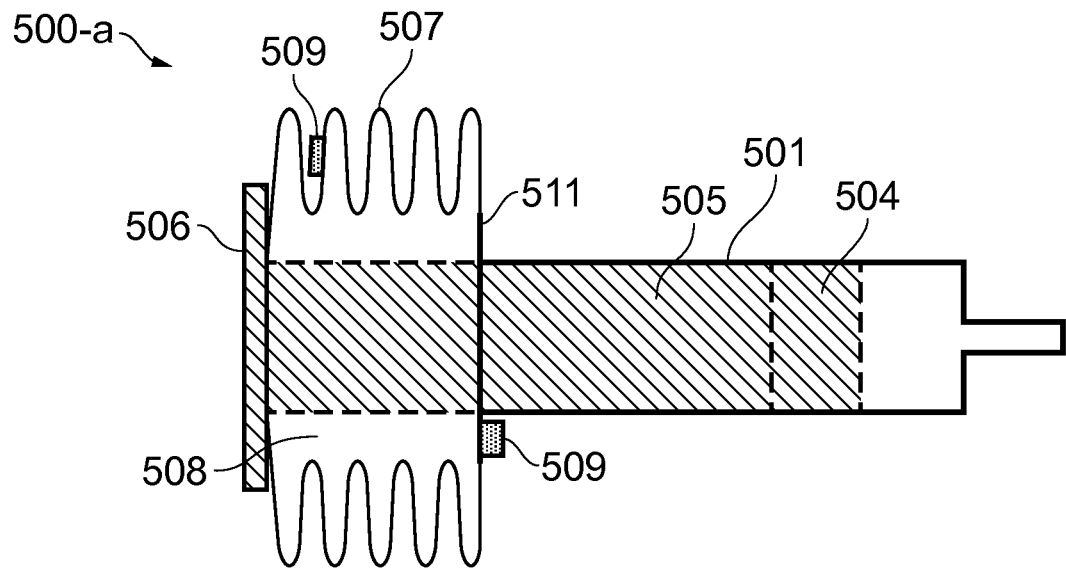
FIGS. 5A and 5B show side views of two exemplary syringes 500-*a* and 500-*b* according to an alternate embodiment of the invention.
Figure 5B:
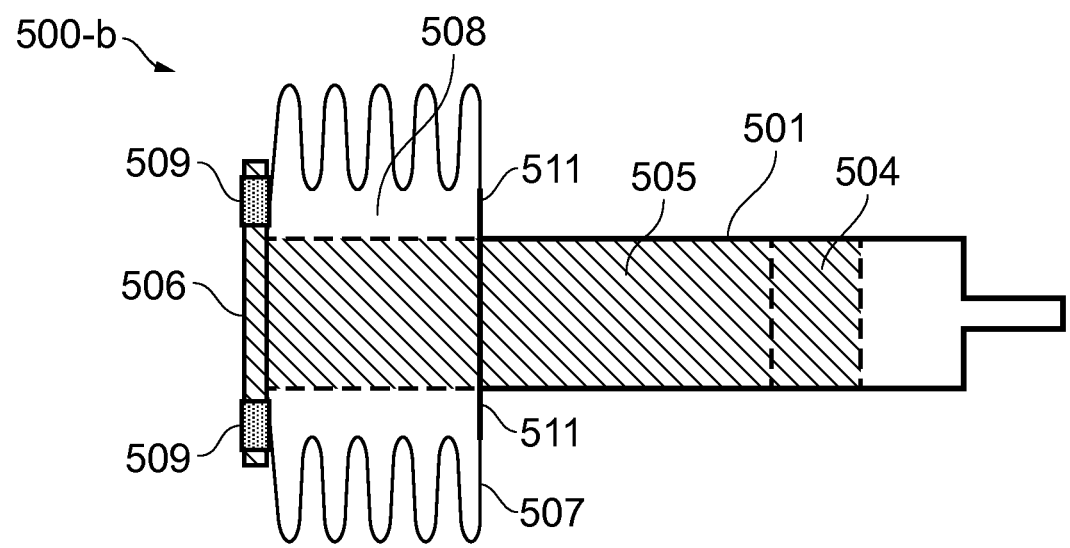

FIGS. 5A and 5B show side views of two exemplary syringes 500-*a* and 500-*b* according to an alternate embodiment of the invention. Each of the syringes 500-*a* and 500-*b* comprise a barrel 501, a barrel flange 511, a plunger 503, a piston 504, a plunger stem 505, a plunger handle 506, a non-sliding seal 507 attached to the barrel 501 and the plunger 503, a sealed volume 508, one or more filters 509 and a sliding seal 510. In this alternate embodiment, the plunger stem 505 includes the piston 504, which provides an assembly that fits snugly within the barrel 501 and is slidably movable within the barrel 501 by using the plunger handle 506. The assembly provides the sliding seal 510 in the barrel 501. As illustrated in FIG. 5A, the filters 509 are located on the non-sliding seal 507 and on the barrel flange 511 of the syringe 500-*a*. As illustrated in FIG. 5B, the filters 509 are located on the plunger handle 506 of the syringe 500-*b*.

Figure 6:
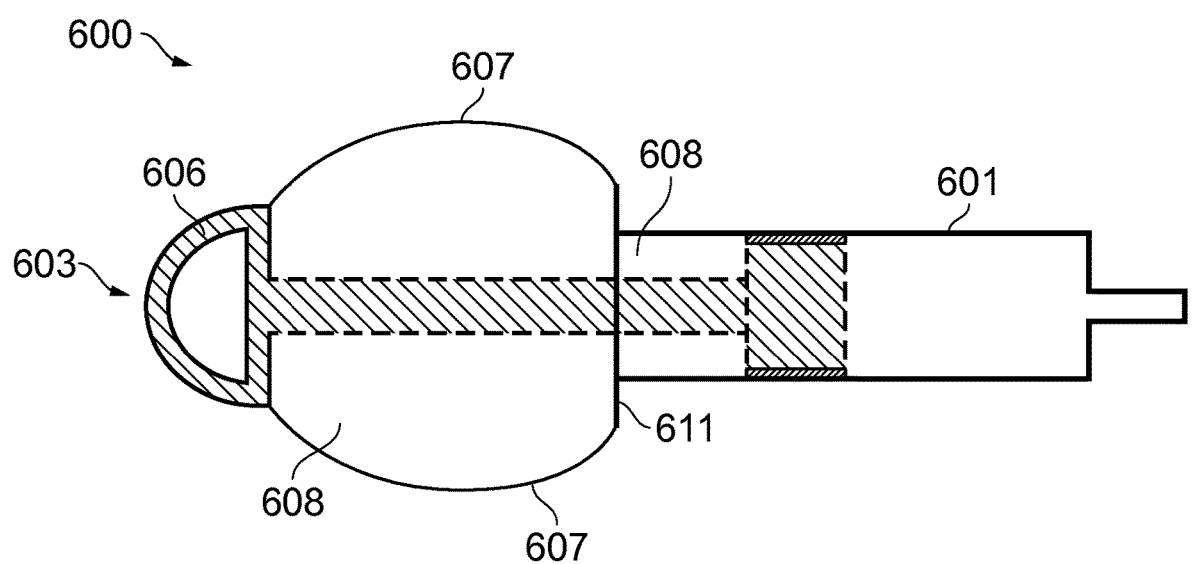
FIG. 6 shows a side view of an exemplary syringe 600 according to another alternate embodiment of the invention.

FIG. 6 shows a side view of an exemplary syringe 600 according to another alternate embodiment of the invention. The syringe 600 comprises a barrel 601, a barrel flange 611, a plunger 603, a plunger handle 606, a non-sliding seal 607 attached to the barrel 601 and the plunger 603, and a sealed volume 608. The syringe 600 is similar to the syringes shown in the first embodiment of the invention as described above in relation to FIGS. 1A, 1B, 4A, 4B and 4C, but differ from them in that the non-sliding seal 607 is formed substantially wholly from a filtering material to allow only filtered or sterilising gases into the sealed volume 608. The filtering material could be for example the material sold under the brand name Tyvek® and can be heat sealed to the plunger 603 on one side and to the barrel 601 at the other side. The features not described are similar to those described in FIG. 1A and FIG. 1B above.

The invention is not to be seen as limited by the embodiments described above, but can be varied within the scope of the appended claims as is readily apparent to the person skilled in the art. For example, in further alternate embodiments, the syringe could be of varying size and volumes. Similarly, the piston assembly could be of varying designs. The syringe could be operable manually or be part of an automatic or semi-automatic system like an auto sampler. The sliding seal could also vary in design and is not limited to bellows or telescopic membranes. The distal end of the syringe could be attached to a sterile tube or a needle through a luer connection or any other technique. The syringe could also be connected to other sterile devices or systems by using a sterile connection device (SCD).

The invention claimed is:
1. A syringe comprising:
a barrel having internal surfaces;
a plunger movable within the barrel;

a non-sliding seal external to the barrel and extending between the barrel and the plunger defining a sealed volume; and at least one filter allowing only filtered gases to enter the sealed volume.

2. The syringe of claim 1, wherein the plunger and the barrel have a sliding seal therebetween.

3. The syringe of claim 1, wherein the non-sliding seal is attached to the barrel, the plunger or both.

4. The syringe of claim 1, wherein the non-sliding seal is in the form of bellows.

5. The syringe of claim 4, wherein the non-sliding seal is telescopic.

6. The syringe of claim 1, wherein the non-sliding seal is made of impermeable material such as silicone or plastics.

7. The syringe of claim 1, wherein at least a portion of the filter is located on or in the non-sliding seal, or the non-sliding seal and filter are integrally formed as one component.

8. The syringe of claim 1, wherein the filter is located on, or is integral with the barrel or the plunger.

9. The syringe of claim 8, wherein the filter comprises a porous material that prevents particulate material and pathogens from entering the sealed volume but permits the passage of gases including sterilizing gases into or out of said volume.

10. The syringe of claim 9, wherein the filter is made of plastics material heat sealable to the non-sliding seal.

11. A method of sterilizing a syringe, the syringe comprising a barrel having internal surfaces;

a plunger movable within the barrel;

a non-sliding seal external to the barrel and extending between the barrel and the plunger defining a sealed volume; and a filter allowing only filtered gases to enter the sealed volume;

wherein the method comprises exposing the internal surfaces to ethylene oxide gas wherein the said gas entering the sealed volume via the filter.

12. A method of maintaining sterility in a syringe wherein the syringe comprises:

a barrel having internal surfaces;

a plunger movable within the barrel;

a non-sliding seal external to the barrel and extending between the barrel and the plunger defining a sealed volume; and a filter allowing only filtered gases to enter the sealed volume;

wherein the method comprises operating the syringe multiple times and maintaining sterility by avoiding the exposure of the internal surfaces other than to syringed liquids and the said filtered gases.

13. The syringe of claim 1, wherein the plunger extends between a proximal plunger end and a distal plunger end, wherein the barrel extends between a proximal barrel end and a distal barrel end, and wherein the non-sliding seal extends from the proximal barrel end toward a proximal plunger end.

14. The syringe of claim 13, wherein the proximal barrel end defines a handle, and wherein the non-sliding seal extends between the proximal barrel end and the handle.

15. The syringe of claim 1, wherein the at least one filter is external to the barrel.

* * * * *